United States Patent
Larson et al.

(10) Patent No.: US 8,251,983 B2
(45) Date of Patent: Aug. 28, 2012

(54) LASER TISSUE FUSION OF SEPTAL MEMBRANES

(75) Inventors: Michael Larson, Colorado Springs, CO (US); Jesse McClure, Colorado Springs, CO (US); Luke Hooper, Norman, OK (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 469 days.

(21) Appl. No.: 12/600,087

(22) PCT Filed: May 14, 2008

(86) PCT No.: PCT/US2008/006261
§ 371 (c)(1),
(2), (4) Date: Nov. 13, 2009

(87) PCT Pub. No.: WO2008/143955
PCT Pub. Date: Nov. 27, 2008

(65) Prior Publication Data
US 2010/0249763 A1 Sep. 30, 2010

Related U.S. Application Data

(60) Provisional application No. 60/917,845, filed on May 14, 2007.

(51) Int. Cl.
*A61B 18/18* (2006.01)
(52) U.S. Cl. ............ 606/8; 606/2; 607/89; 607/88
(58) Field of Classification Search ........... 606/8, 2; 607/89, 88
See application file for complete search history.

(56) References Cited

U.S. PATENT DOCUMENTS

| 4,672,969 | A | | 6/1987 | Dew |
| 4,854,320 | A | * | 8/1989 | Dew et al. ............ 606/3 |
| 5,071,417 | A | | 12/1991 | Sinofsky |
| 5,156,613 | A | | 10/1992 | Sawyer |
| 5,272,716 | A | | 12/1993 | Soltz et al. |
| 5,300,065 | A | | 4/1994 | Anderson |
| 5,334,191 | A | | 8/1994 | Poppas et al. |

(Continued)

OTHER PUBLICATIONS

Athiraman, Hemanth, et al., "Selective photothermal tissue interaction using 805-nm laser and indocyanine green in tissue welding," Journal of X-Ray Science and Technology 12 (2004), pp. 117-126.

(Continued)

*Primary Examiner* — Kinam Park
(74) *Attorney, Agent, or Firm* — Dorsey & Whitney LLP

(57) ABSTRACT

A laser tissue fusion device is optimized for particular surgical applications to join tissue layers. The device has two opposed arms that engage and disengage to clamp and release layers of tissue therebetween. The distal end of the first arm is disposed opposite the distal end of the second arm. A laser energy source generates therapeutic laser energy is either integrated within the device is a separate unit. An energy pathway transmits the laser energy to the distal end of the first arm to deliver the laser energy to tissue layers clamped between the distal ends of the arms. An actuator decreases the separation distance between the distal ends of the arms to clamp the tissue layers and activates the laser energy source upon engagement. The laser energy source delivers a burst of energy at a predetermined wavelength for a predetermined period of time sufficient to spot weld the tissue.

30 Claims, 7 Drawing Sheets

U.S. PATENT DOCUMENTS

| | | |
|---|---|---|
| 5,336,221 A | 8/1994 | Anderson |
| 5,364,389 A | 11/1994 | Anderson |
| 5,409,481 A | 4/1995 | Poppas et al. |
| 5,468,238 A | 11/1995 | Mersch |
| 5,824,015 A | 10/1998 | Sawyer |
| 6,024,743 A | 2/2000 | Edwards |
| 6,176,854 B1 | 1/2001 | Cone |
| 6,551,302 B1 * | 4/2003 | Rosinko et al. ............. 604/505 |
| 6,626,901 B1 | 9/2003 | Treat et al. |
| 6,849,075 B2 | 2/2005 | Bertolero et al. |
| 7,025,764 B2 | 4/2006 | Paton et al. |
| 7,077,839 B2 | 7/2006 | Hamblin et al. |
| 7,078,378 B1 | 7/2006 | Owen et al. |
| 7,094,252 B2 | 8/2006 | Koop |
| 7,160,299 B2 | 1/2007 | Baily |
| 7,255,770 B2 | 8/2007 | Wissman |
| 2001/0051800 A1 | 12/2001 | Eugeny et al. |
| 2003/0204182 A1 | 10/2003 | Ahle et al. |
| 2005/0119643 A1 | 6/2005 | Sobol et al. |

OTHER PUBLICATIONS

Flock, Stephen T., Ph.D., et al., "Progress Towards Seamless Tissue Fusion for Wound Closure," Otolaryngol. Clin. N. Am. 38 (2005), pp. 295-305.

Grummet, Jeremy P., et al., "Laser Welded Vesicourethral Anastomosis in an In vivo Canine Model: A Pilot Study," The Journal of Urology, vol. 168, Jul. 2002, pp. 281-284.

Lobik, Leonid, et al., "Bladder Welding in Rats Using Controlled Temperature $CO_2$ Laser System," The Journal of Urology, vol. 161, May 1999, pp. 1662-1665.

* cited by examiner

LASER TISSUE FUSION OF SEPTAL MEMBRANES

BACKGROUND

Since the late 1980's, laboratory research has indicated the potential of using lasers to "weld" biological tissues together, sometimes facilitated by introducing an albumen solder. Many encouraging results have been obtained, suggesting that lasers hold promise for instant wound closure. An important advantage is achieving an instant, watertight bond. While some laser systems have been developed for use in surgical applications, none has been able to realize a practical system that offers a comparative advantage to standard procedures. This is due primarily to two factors: the systems have attempted to provide general applicability for multiple tissue types, i.e., a one-size-fits-all approach, and the systems require users to exercise a significant amount of experience and skill in detecting changes in tissue appearance while using the laser. In particular, it has been found that different tissues require different sets of laser parameters, e.g., wavelength, pulse duration, power level, exposure time, and pressure. An additional drawback is that, even with optimized performance parameters, use of these test systems is an "art," requiring an inordinate amount of experience on the part of the operator, despite attempts to automate the feedback and control of the laser devices. Thus, it is easy to burn tissue or end up with an incomplete tissue weld.

During surgical procedures to correct nasal septal deviation—nasal cavity blockage linked to chronic sinusitis and other conditions—bone and cartilage are removed from the centerline of the nose, while preserving the mucoperichodrial flaps covering both sides. These flaps must be brought back together, a procedure called "coaptation." This prevents blood clotting in-between and hematoma formation. Coaptation must be completed to ensure the survival of septal cartilage. If the flaps are not re-joined, the blood supply will be reduced, killing the remaining cartilage and causing serious, irreversible saddle nose deformity wherein a patient's nose collapses.

Currently coaptation of the tissue membranes lining the septum is accomplished with a needle and suture, stapling, or by intranasal packing. The current suturing method comes with a number of serious shortcomings, including difficulty visualizing and guiding the needle deep in the nasal cavity when working through the nostrils, inadvertent tearing of the vascular nasal wall by the needle (with resultant bleeding leading to immediate visualization problems and to later scarring and healing problems through the development of nasal synechia), and the possibility of breaking or detaching the needle (requiring a radiological scan to ensure removal of all fragments). Stapling can similarly cause bleeding problems with similar side effects. Both suturing and stapling can result in sub-optimal coaptation due to a lack of uniformity in closure. This current suture coaptation method also consumes a relatively long time in the operating room.

The other method currently used, i.e., inserting intranasal packing, is not a benign procedure. In addition to causing discomfort for patients (the material is left in the nose for 24 to 72 hours), studies show that the intranasal packing reduces oxygen saturation and can lead to toxic shock syndrome. In addition to packing, flat splints are often placed in the nostrils on each side of the septal wall to prevent fibrous growth that could potentially cause nasal synechia as a result of a needle tearing and pushing or pulling mucosa cells into the nasal cavity during suturing.

Repairing and grafting nerves and blood vessels using a microscope present many difficulties for traditional surgical closure techniques, e.g., sutures, staples, and clips. The small size of the tissues involved necessitate specialized thread and needles. For conventional procedures, suture with a diameter on the order of 0.1 mm is common. Microsurgical procedures can require suture two orders of magnitude smaller, down to 0.001 mm. Surgeons must train extensively to compensate for hand tremor, which is significant given the small structures to be joined.

The information included in this Background section of the specification, including any references cited herein and any description or discussion thereof, is included for technical reference purposes only and is not to be regarded subject matter by which the scope of the invention is to be bound.

SUMMARY

A laser tissue fusion device joins layers of tissue in surgical procedures. The laser septal closure device overcomes the problems described above by optimizing the performance and simplifying use through dedication to single applications. Because the laser tissue fusion device is optimized for particular surgical applications for joining tissue layers, the device thus overcomes the barriers that have prevented others from creating an economically viable laser fusion solution. The laser tissue fusion device may be pre-set to the optimal performance characteristics for the particular tissue involved and packaged in an easy to use device. The joining of tissue layers is accomplished through the controlled application of laser heating and pressure to induce protein denaturation and subsequent tissue fusion, through renaturation and intertwining, across the interface between tissue layers. The device can be used to provide an immediate, water-tight closure to wet or dry wounds. This can facilitate accelerated healing.

The laser tissue fusion device has two opposed arms that may be engaged and disengaged to clamp and release layers of tissue therebetween. The distal end of the first arm is disposed opposite the distal end of the second arm. A laser energy source that generates therapeutic laser energy is provided either integrated within the body of the device or as a separate unit connected to at least one of the arms. An energy pathway transmits the therapeutic laser energy from the laser energy source to the distal end of the first arm to deliver the therapeutic laser energy to tissue layers clamped between the distal ends of the arms. The energy pathway may be in the form of an optical fiber. An actuator is configured to decrease the separation distance between the distal end of the first arm and the distal end of the second arm upon engagement and thereby clamp the tissue layers between the distal ends of the arms. The actuator is further configured to activate the laser energy source when the tissue layers are clamped between the arms. Pressure between the arms is governed by the actuator mechanism, which is limited to prevent excess clamping force on the tissue. The laser energy source further delivers a burst of energy at a predetermined wavelength for a predetermined period of time sufficient to spot-weld the portion of tissue between the ends of the arms. The distal end of the first arm may have an angled mirror and/or a lens to direct and focus the laser energy from the energy pathway into the tissue. The distal end of the second arm may be mirrored to reflect any laser energy passing through the tissue back into the tissue.

In one implementation, a laser tissue fusion device is optimized for surgical procedures involving the nasal septum (the internal, mid-line of the nose), namely coaptation of mucoperichondrial membranes (septal mucosa). The laser tissue fusion device is a superior alternative to the current method of coaptation using suture. The device eliminates the shortcomings described above by permitting a surgeon to quickly, and with one hand, "spot weld" the mucoperichondrial flaps. Each of the arms of the laser fusion device is configured to fit within respective nostrils of the patient and engage the septal mucosa. The laser tissue fusion device provides several benefits for both patients and doctors including improved visualization, no tearing of the lateral nasal wall and subsequent development of synechia, no broken needles, and reduced surgical time. The device may also find application in rhinoplasty where nasal cartilage is harvested for reconstructive purposes, and surgeries requiring access to the base of the skull employing a transsphenoidal approach, i.e., moving the septum, such as to access the pituitary.

In another implementation, a laser tissue fusion device is optimized for endoscopic surgical procedures. The arms of the device may be mounted at the distal end of a tube, trochar, or other endoscopic device. A handle at the proximal end may have an actuator to manipulate the second arm to clamp or unclamp layers of tissue between the arms. The actuator is further configured to activate the laser energy source when the tissue layers are clamped between the arms. The device permits a surgeon to quickly, and with one hand, "spot weld" the layers or flaps of tissue within the surgical field. For example, the endoscopic device may be useful in colorectal and gastric bypass surgeries for fusing tissue folded against itself.

In another implementation, small laser tissue fusion devices may be optimized for use in microsurgical applications. Laser fusion devices provide a huge benefit since there is no relative motion required during joining as is needed between the tissue and a needle/suture. The surgeon can ensure proper positioning of the tissue layers before actuating a spot-welding laser, which has integrated tissue-holding arms or fixtures to approximate the tissue to be joined.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

DETAILED DESCRIPTION

Septal Fusion Implementations

A laser tissue fusion device according to the implementations described in further detail below may be used to "spot weld" layers of tissue together. A primary application of one implementation of the laser tissue fusion device may be in septoplasty operations. These are common surgical procedures which correct nasal septal deviation—nasal cavity blockage linked to chronic sinusitis and other conditions. Bone and cartilage are removed from the centerline of the nose, while preserving the mucoperichodrial flaps covering both sides. The flaps must be brought back together, "coapted," to prevent blood clotting in between (i.e., hematoma formation). If the flaps are not re-joined, the blood supply will be reduced, killing the remaining cartilage and causing serious, irreversible saddle nose deformity wherein a patient's nose collapses. This implementation of a laser tissue fusion device may also find application in rhinoplasty where nasal cartilage is harvested for reconstructive purposes. This implementation of the laser tissue fusion device may further be used during surgeries requiring access to the base of the skull employing a transsphenoidal approach, i.e., moving the septum, such as to access the pituitary.

Figure 1:
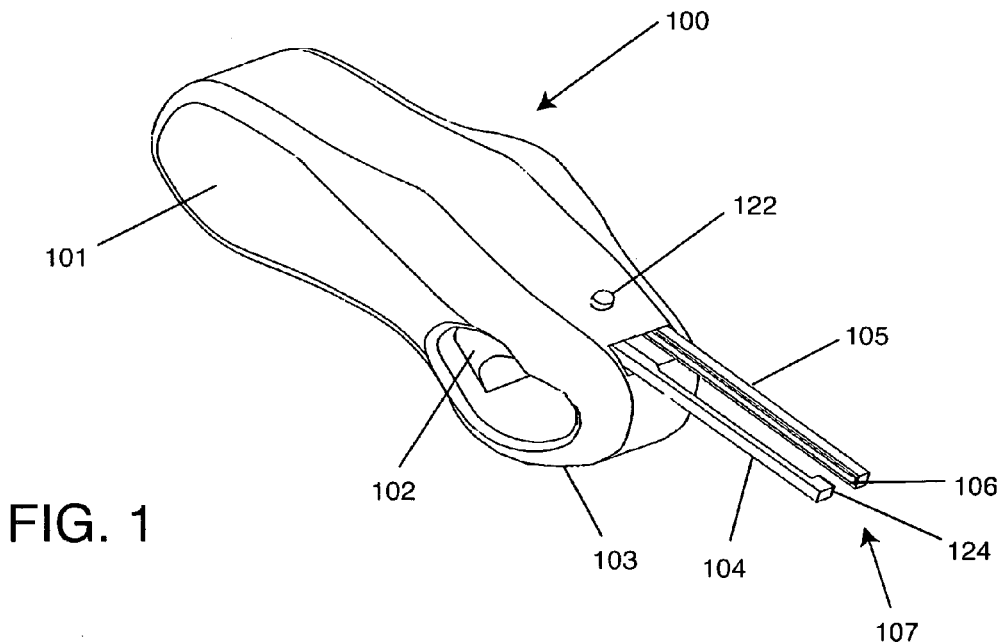
FIG. 1 is an isometric view of an exemplary embodiment of a laser tissue fusion device designed principally for fusion of septal tissue.

FIG. 1 depicts an exemplary implementation of a handheld laser tissue fusion device 100 designed principally for nasal operations. The device 100 may have a housing 101 in the form of a handle which supports a mechanical actuator such as a trigger 102. The trigger 102 may be shielded from inadvertent actuation by a trigger guard 103 formed as part of the handle housing 101. The housing 101 and the trigger 102 may be formed of molded plastics or other polymers to provide a desirable ergonomic feel for the clinician.

The device 100 further includes a motile arm 104 and a static arm 105. In this embodiment, the static arm includes a laser energy output 106 and houses a pathway (not shown) for delivering the laser energy from a laser energy source to the output 106. The arms extend distally from the handle 102 and may be oriented generally parallel with each other. The arms 104, 105 are substantially the same length and extend substantially the same distance from the handle 101 to their distal ends 107. The separation distance between the distal ends 107 of the arms 104, 105 may be selected to conform to a typical spacing between the nostrils of a patient to allow the distal ends 107 of the arms 104, 105 to be easily inserted into the nostrils. In some embodiments the spacing between the arms 104, 105 may be adjustable and, in other embodiments, different handle configurations may be designed to provide a range of spacing between the distal ends 107 of the arms 104, 105. A visual indicator, for example a light emitting diode 122 (LED) may be mounted on the handle 101 to indicate when laser energy is being output from the device 100. Alternative indicators could be used, for example an audible signal could be generated.

Figure 2:
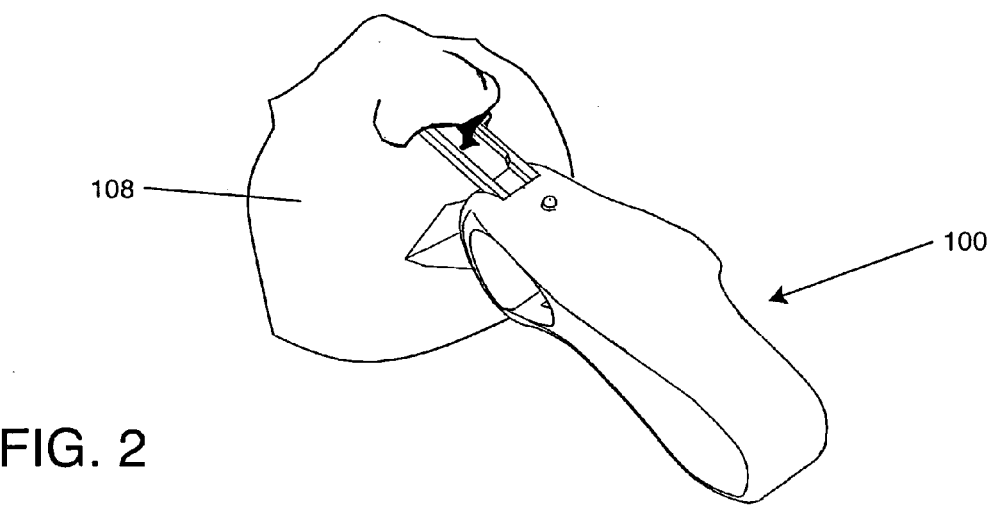
FIG. 2 is an isometric view of the laser tissue fusion device of FIG. 1 with the arms of the device in place for use during nasal surgery.

FIG. 2 depicts a laser tissue fusion device 100 in use in the treatment of a patient 108 for septal closure. The distal ends of each of the arms 104, 105 are inserted within respective nostrils of the patient 108 to reach opposing positions on each side of the septal mucosa.

Figure 3:
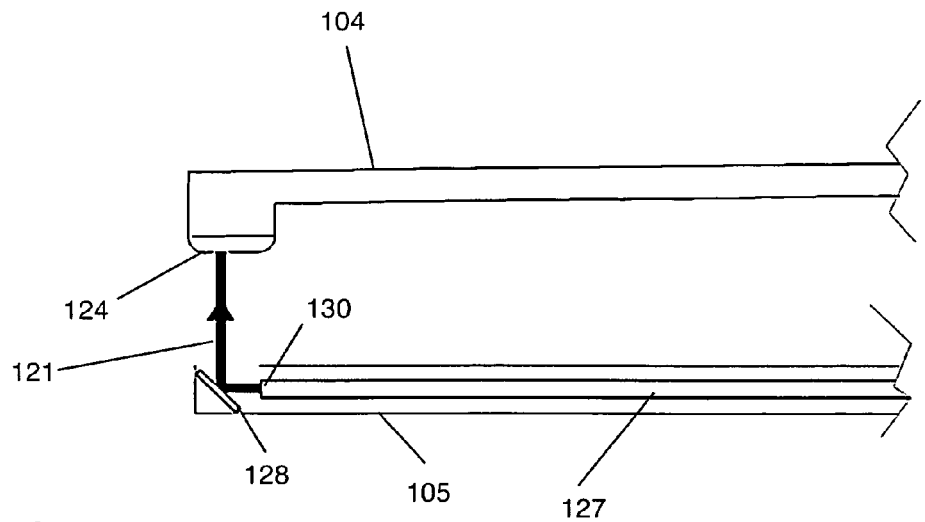
FIG. 3 is a cross section of a detail of the distal tips of the arms of the laser tissue fusion device of FIG. 1 in an actuated state.

FIG. 3 depicts a manner by which the laser energy 121 leaves the device 100 to act upon the tissue. A fiber optic cable 127, composed of one or more small strands, carries the laser energy 121 from the laser energy source, e.g., a laser diode contained within the handle or a laser source located in a stand-alone unit. The fiber optic cable 127 is mounted in the static arm 105. A reflector 128 is positioned near an aperture of the fiber optic cable 127 and directs the emanating beam of laser energy 121 toward the tissue lying between the two arms 104, 105. In one embodiment, a lens (not shown) may be introduced between the aperture 130 and the reflector 128 or between the reflector 128 and the tissue to focus the laser energy 121. A reflective surface 124 is formed on the distal end of the motile arm 104 aligned with the path of the laser energy 121 redirected by the reflector 128. The reflective surface 124 acts to prevent any laser energy 121 that penetrates the tissue entirely from irradiating undesired tissue locations by reflecting the laser energy 121 back to the same tissue location receiving the incident laser energy.

Figure 4:
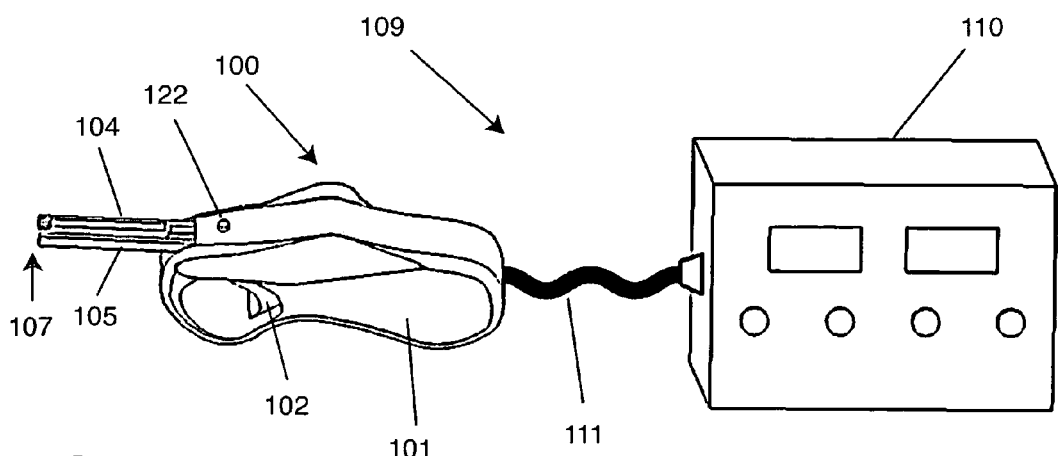
FIG. 4 is a schematic view of an exemplary embodiment of a disposable hand-held laser tissue fusion device connected to a reusable laser energy source by a fiber optic cable.

FIG. 4 depicts one implementation of laser tissue fusion system 109 with a handheld tissue fusion device 100 and a separate, reusable laser energy source 110. The laser energy source 110 is connected to the device 100 by an umbilical 111. The umbilical 111 may be composed of a fiber optic cable for transmitting the laser energy from the laser energy source 110 and one or more electrical wires for the control of the laser energy source 110. A control system in the laser energy source is actuated by signals in the electrical wires upon actuation of the trigger 102 and controls the power and duration of the laser energy output from the laser diode 118 at a level and for a period optimized to fuse the tissue layers. The laser energy is transmitted from the laser energy source 110 via the umbilical 111, which connects with the fiber optic cable (see FIG. 3) in the handle 101 and travels through the static arm 105 to the laser output at the distal end 107. The LED 122 provides a visual indication during the application of the laser energy and is deactivated after the duration of energy application is complete to indicate to the clinician that the fusion is complete and that the device 100 may be disengaged from a clamped position for relocation to fuse another area of tissue or that the device 100 may be removed.

Figure 5:
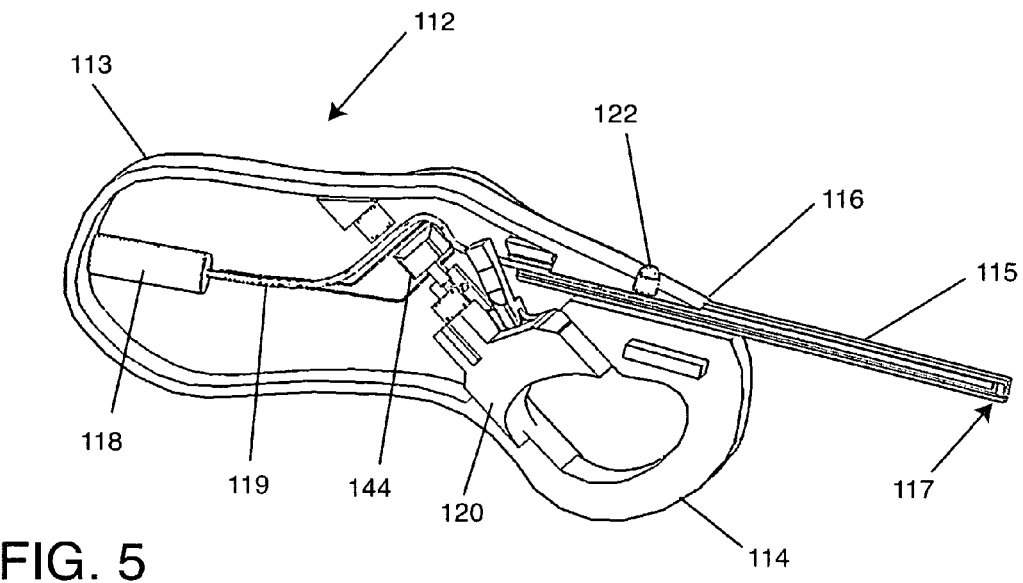
FIG. 5 is an isometric view in cross section of an alternative embodiment of a laser tissue fusion device with a laser energy source within the handle.

FIG. 5 depicts a compact implementation of a laser tissue fusion device 112 in a cross-section view wherein one side of the handle 113 is shown. As in implementations previously described, the handle 113 of the device 112 forms a trigger guard 114 to shield a trigger 120 or actuator. A static arm 115 and a motile arm (not shown) each extend parallel distally from the handle 113 to a distal end 117 where the laser energy is output from the static arm 115. In this embodiment, the handle 113 may be reusable while the static arm 115 and the motile arm (not shown) may be disposable or reusable after sterilization. As shown in FIG. 5, the static arm 115 is held at its proximal end within a receptacle 116 in the handle 113 and may be removed therefrom and replaced. The motile arm (not shown) is similarly held in a receptacle from which it can be removed and replaced.

The laser energy source in this embodiment may be generated by a laser diode 118 housed within the handle 113 and powered by a replaceable or rechargeable power source, e.g., a battery (not shown). Laser power generation is initiated by actuation of a switch 144 by the motion of the trigger 120. A control system (not shown) controls the power and duration of the laser energy output from the laser diode 118 at a level and for a period optimized to fuse the tissue layers. Again, the LED 122 may provide a visual indication of the duration of the application of the laser energy. The therapeutic laser energy output from the laser diode 118 is directed to the distal end of the static arm 115 via an energy pathway 119 upon actuation of the trigger 120. The energy pathway 119 may be formed inside the handle 113 by a series of mirrors or reflective surfaces that direct the laser energy within the handle 113 to be transmitted within the static arm 115 to the point of laser output at the distal end 117. Alternatively, the energy pathway 119 may be a fiber optic cable.

Laser energy sources of various wavelengths can be used, as many will impart a sufficient amount of useful photothermal energy to tissue. A number of wavelengths may be used, for example, 808 nm, 830 nm, 1060 nm, 1220 nm, 1430 nm, and 10.6 μm wavelengths. The size of the laser spot can likewise be varied. A nominal diameter on the order of 1 mm to 5 mm is appropriate for the coaptation of nasal mucosa. Success can be achieved for a range of beam power levels impinging on the tissue, in particular between 500 mW to 5 W works well. The dwell time needed to form a sufficient tissue to tissue bond is inversely related to the power density of the beam, which is a combination of the spot size and power, and is typically between 10 W/cm$^2$ and 100 W/cm$^2$. Success can be achieved with various times, but between 1 sec and 10 sec has been found to work well in this application. The total energy deposited on the tissue varies with the chosen wavelength, and typically ranges from 50 J to 500 J.

Figure 6:
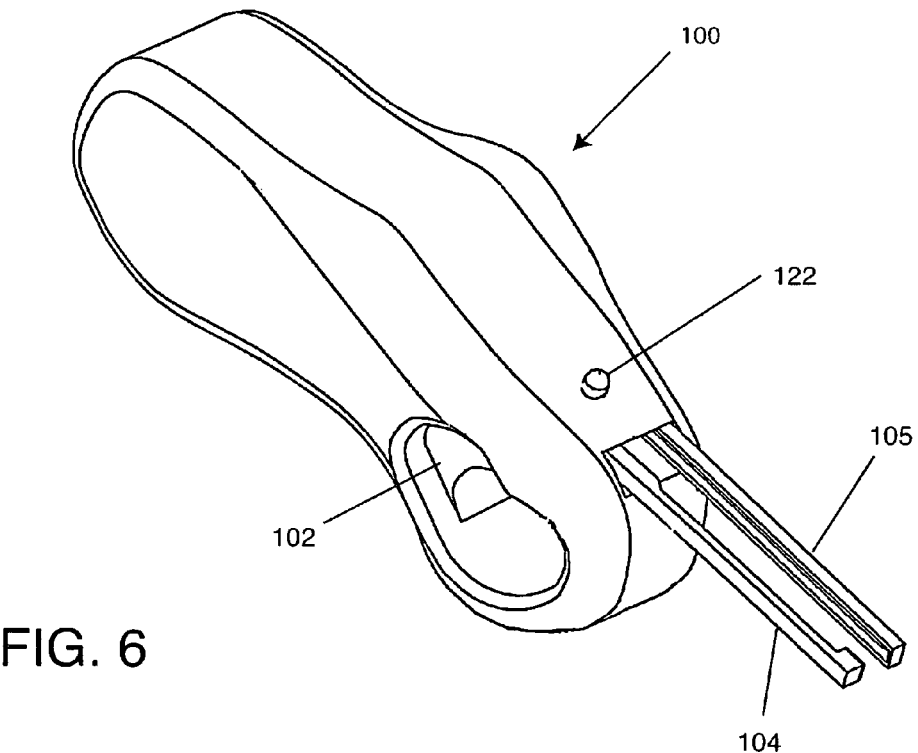
FIG. 6 is an isometric view of the laser tissue fusion device of FIG. 1 in a pre-actuated state.
Figure 7:
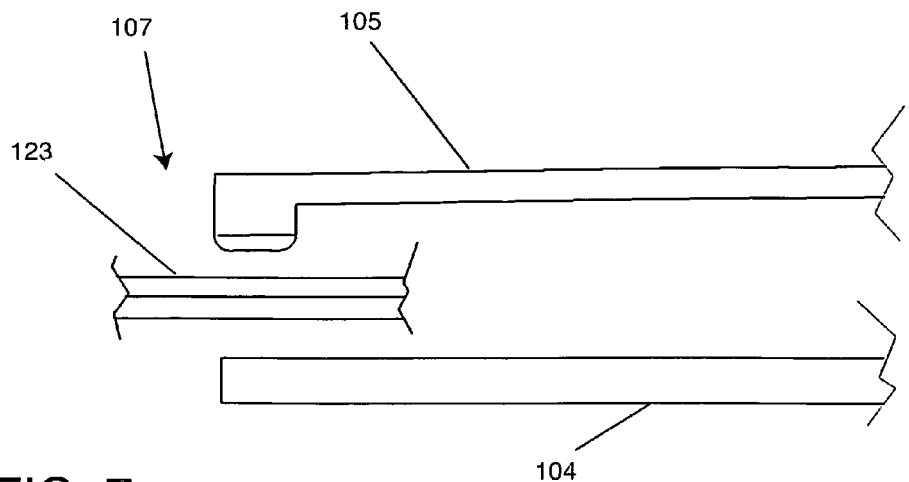
FIG. 7 is a side elevation view of a detail of the arms of the laser tissue fusion device in the pre-actuated state of FIG. 5 with layers of tissue positioned between the arms.
Figure 8:
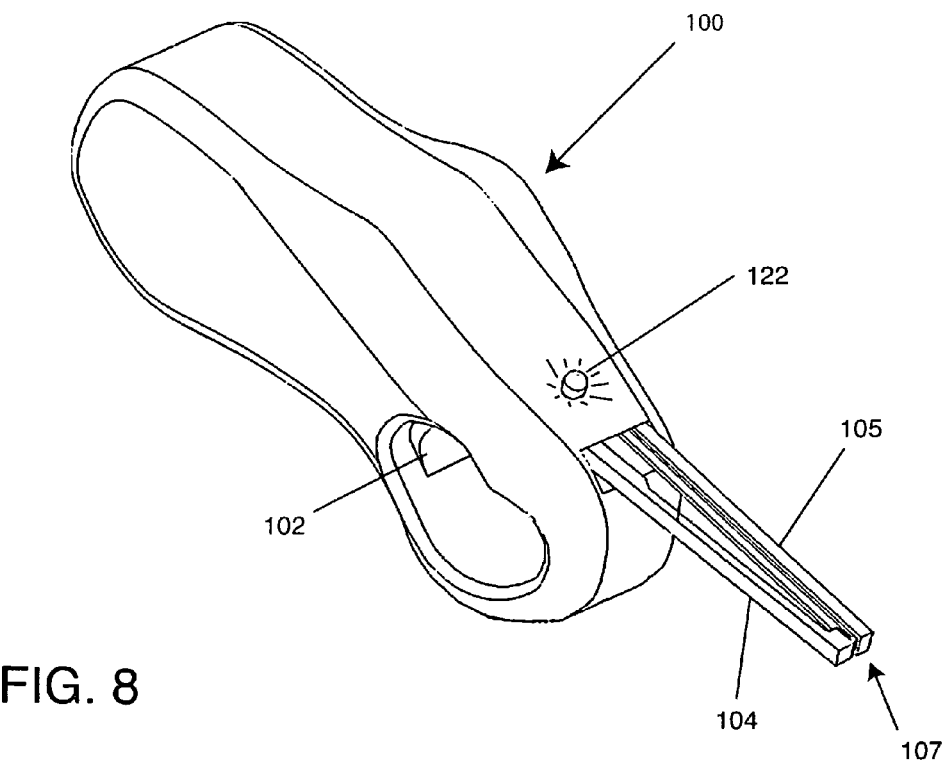
FIG. 8 is an isometric view of the laser tissue fusion device of FIG. 1 in an actuated state.
Figure 9:
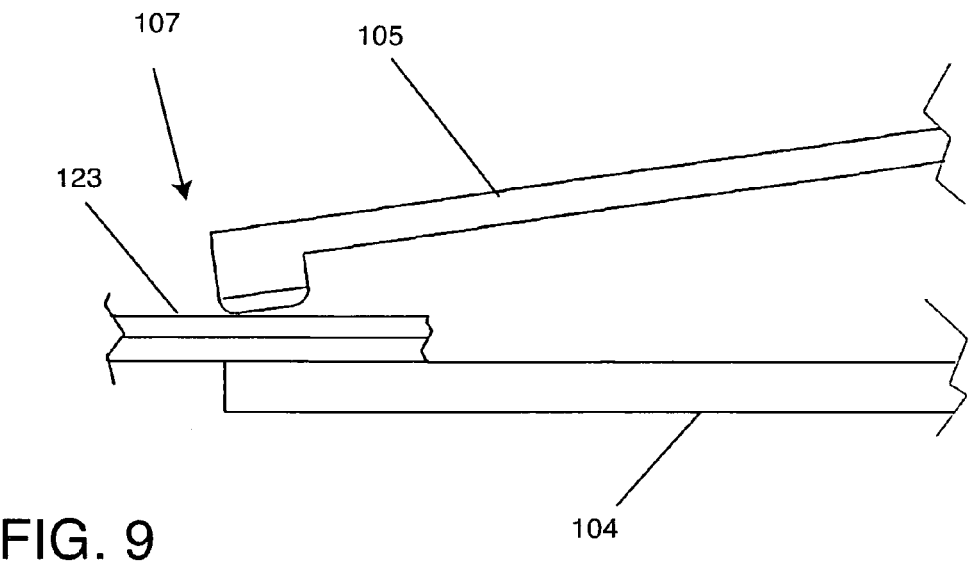
FIG. 9 is a side elevation view of a detail of the arms of the laser tissue fusion device in the actuated state of FIG. 7 with layers of tissue clamped between the arms.

FIG. 6 depicts the device 100 in a disengaged position. The trigger 102 is not actuated, the arms 104, 105 are open and spaced apart, the LED indicator 122 is off, and there is no laser emission. FIG. 7 shows the distal ends 107 of the arms 104, 105 straddling layers of tissue 123 to be joined. Comparatively, FIG. 8 depicts the device 100 in an actuated or engaged position. The trigger 102 is depressed, the arms 104, 105 are closed, the LED indicator 122 is on, and laser energy is emitted at the distal end 107. FIG. 9 shows the distal ends of the arms 104, 105 pinching or clamping layers of tissue 123 to be joined with laser energy applied to the tissue between the distal ends 107 of the arms 104, 105.

Figure 10:
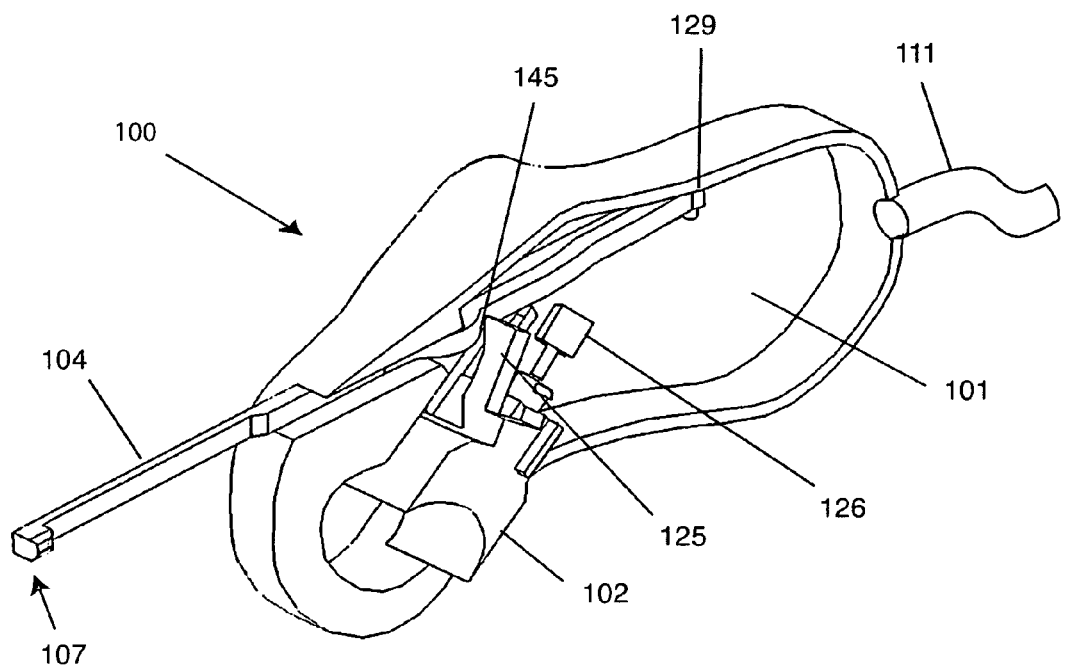
FIG. 10 is an isometric view in cross section of the laser tissue fusion device of FIG. 1 in a pre-actuated state.

FIG. 10 depicts the device 100 in cross section in a disengaged position to provide an example of a structure for motivating the motile arm 104 to deflect toward the static arm 105 (not shown) by rotating on a hinge connection 129 at a proximal end of the motile arm 104 housed within the handle 101. In FIG. 10, the trigger 102 is not depressed and the arms 104, 105 are open at their maximum separation distance. As shown, the trigger 102 may be constructed with a wedge-shaped portion 125 that, when in the disengaged position, rests against a cam surface 145 of the motile arm 104 and holds the motile arm 104 against the inside wall of the housing 101. FIG. 10 also depicts an example of trigger actuation detection. A switch 126 is mounted inside of the housing 101 behind the trigger 103. Since there is no contact between the trigger 102 and the switch 126, the laser energy source is inactive.

Figure 11:
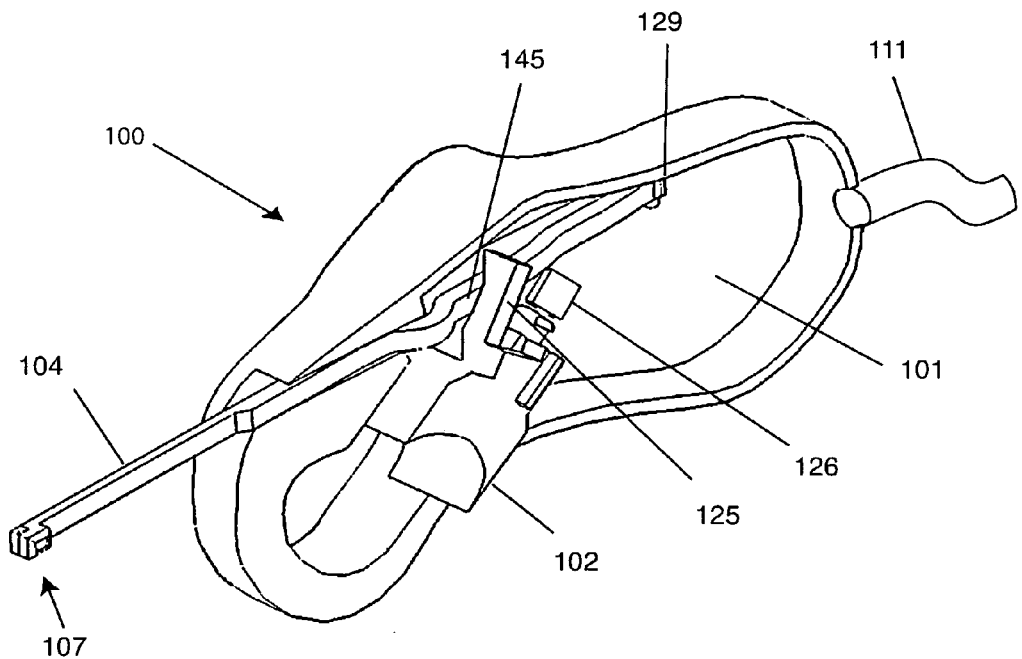
FIG. 11 is an isometric view in cross section of the laser tissue fusion device of FIG. 1 in an actuated state.

Comparatively, FIG. 11 depicts the same embodiment of the device 100 in cross section as in FIG. 10, but in an actuated position. The trigger 102 is depressed against the force of a spring (not shown; positioned in the other half of the handle 101) and the arms 104, 105 (not shown) are closed, i.e., the separation distance between the distal ends 107 of the arms 104, 105 is reduced. When the trigger 102 is depressed, the wedge-shaped portion 125 moves behind the cam surface 145 and permits the movement of the motile arm 104 toward the static arm 105 about the hinge connection 129 under the action of a spring positioned between the housing 101 and the motile arm 104 (not visible). This causes the distal end 107 of the motile arm 104 to deflect laterally toward the distal end 107 of the static arm 105 (not shown), i.e., the distal end 107 of the motile arm 104 moves generally normal to its length. When the arms 104, 105 are positioned in either side of the nasal cavity, the deflection of the motile arm 104 holds the arms 104, 105 in close proximity to each other and against the septal tissue with a preset force.

When the trigger 102 is depressed, it also makes contact with the switch 126 causing the laser energy source to turn on for a determined amount of time under the control of a timing circuit. The switch 126 is connected to the external laser energy source by the umbilical 111 (connection not shown; positioned in the other half of the handle 101). The laser then fires at a preset intensity for a preset duration according to the circuit after which the arms 104, 105 may be released by releasing the trigger 102. When the trigger 102 is fully depressed, it may be detected by a contact sensor on the switch 126 that interfaces with the back of the trigger 102 when the trigger 102 is fully depressed. The switch 126 signals the circuit to fire the laser for a set time period that is visually indicated by the LED 122. If the trigger 102 is released before the laser firing time period has ended, the lack of contact with the contact sensor on the switch 126 may be detected by the circuit, which may automatically shut off the laser as a safety measure.

In an alternate implementation, the trigger mechanism may be designed to cause both arms to move and pinch together against the septal tissue. Such a configuration may be achieved, for example, by constructing the trigger with a pair of linear cams to interface with each of the arms. This embodiment may be desirable in order to ensure that equal pressure is applied to both sides of the septal wall. However, since the arm housing the laser pathway is no longer stationary, the angles of any reflective surfaces forming the pathway may have to be adjusted as appropriate to accommodate the angle of the arm.

In another implementation, the distal ends of the arms may be pressed toward each other by a set of compression springs within the handle. The springs may be chosen to provide a desired force and move the distal ends of the arms toward each other to pinch the septal tissue together without physically damaging the tissue. The tissue may then be fused together with the laser energy.

In a further implementation, movement of the arms may be electrically actuated upon pressing the trigger. For example, a solenoid in the handle may be actuated to cause the motile arm to move toward the static arm (or to cause both arms to move together). A timing circuit may be used to trigger the solenoid to return to its inactive position after a set period of time corresponding to clinical efficacy of the laser. The solenoid may further be adjusted to change its travel distance to increase or decrease the separation distance between the distal ends of the arms depending upon the particular thickness of the patient's septum. This thickness may be measured in advance of the procedure to allow adjustment of the solenoid to a proper setting.

Fusion Methodologies

A method of performing coaptation of the mucoperichondrial flaps in nasal septal tissue may comprise the following operations. First, the septal tissue is pressed together from opposite sides accessed through the nostrils of a patient. This pressure may be applied by pulling the trigger and closing the arms of the laser fusion device. Next, therapeutic laser energy is applied to the septal tissue for a period of time sufficient to fuse the septal tissue. The laser energy is actuated upon actuation of the trigger, which simultaneously applies the pressure to the septal tissue. Once a therapeutic time has elapsed and the flaps have been welded together the laser energy ceases and the pressure on the septal tissue may be released. Depending upon the area of the flaps that require coaptation, this method may be repeated several times at different locations on the septal tissue to "spot weld" the tissue together. Generally, 6-8 spots of about 2 mm diameter are sufficient to hold the septal mucosa together and avoid the need for nasal packing. Additionally, the need for splints is removed because there is little possibility of creating nasal synechia within the nasal cavity as may occur when suturing.

One reason this methodology is effective in the application to septal mucosa is that clinical studies have shown that human mucoperichodrial flaps are remarkably consistent in thickness (on the order of 1 mm each side or 2 mm total) across race, gender, and size of individual. Therefore, the thickness of the septal mucosa is not a significant variable to consider when determining the optimal power and application time to achieve fusion. Thus, a single set of therapeutic parameters can be set for the device to achieve optimal results for any individual with no need for experience or skill in laser fusion on the part of the clinician.

This method of coapting mucoperichondrial flaps has been demonstrated in advance of clinical trials through benchtop experiments on representative tissue systems. These experiments are designed to the optimal combination of performance parameters, e.g., laser wavelength, duration of irradiation, laser power level, and mechanical pressure, to achieve tissue fusion. A benchtop testing device provides controlled tests on representative tissue models. The model membranes (i.e., possessing similar material properties to the collagen-rich lamina propria and periosteum, which underlie the mostly squamous epithelial cells of the mucoperichondrial flaps) employed in initial testing may include AlloDerm®. AlloDerm® is commercially available, donated human tissue that has been processed to remove all epidermal and dermal cells, while preserving the remaining biological dermal matrix. Additionally, laser fusion on harvested horse septal mucosa has been performed successfully.

A membrane support table may be used to hold layers of tissue in proximity to one another and positioned between the jaws of the benchtop testing device. Compression induced between the jaws in tissue membranes may be controlled with a rack and pinion plunger and measured with a load cell. The membrane in the support table may be wetted as needed to more closely simulate in vivo conditions. The strength of the resulting tissue bonds may be analyzed in a mechanical pull test and under a microscope. Experimental results under a variety of conditions using horse mucosa is presented in the table below.

| Wavelength (nm) | Duration (s) | Arm Force (lbs) | Power (W) | Fusion Effect | Visual Appearance |
|---|---|---|---|---|---|
| 808 | 5 | 1.5 | 1.7 | None | No Discoloration |
| 808 | 10 | 1.5 | 1.7 | None | No Discoloration |
| 808 | 10 | 1.5 | 3.2 | None | No Discoloration |
| 808 | 30 | 0.5 | 2.5 | Minimal | Slight Discoloration |
| 808 | 60 | 1 | 2 | Minimal | Slight Discoloration |

-continued

| Wavelength (nm) | Duration (s) | Arm Force (lbs) | Power (W) | Fusion Effect | Visual Appearance |
|---|---|---|---|---|---|
| 808 | 60 | 0.5 | 2.5 | Excellent | Slight Discoloration |
| 808 | 60 | 0.5 | 3 | Excellent | Burned Tissue |
| 915 | 30 | 0.5 | 2.4 | None | No Discoloration |
| 915 | 60 | 0.5 | 2.4 | None | Slight Discoloration |
| 1064 | 30 | 0.5 | 2.5 | None | No Discoloration |
| 1064 | 66 | 0.5 | 2.5 | Minimal | Slight Discoloration |

Three different wavelengths of laser light energy at different power levels were used in this exemplary experimental series. The duration of the laser energy application and the force holding the tissue layers together were also varied. In actual practice, the force applied to hold the tissue membranes together was insignificant as long as the membranes were in physical contact with each other at the weld spot. As indicated, laser energy applied to tissue layers at a wavelength of 808 nm, at 2.5 W of power, and for a period of 60 seconds produced the best results (i.e., excellent adhesion with minimal tissue necrosis) in this experimental series with horse mucosa. Additional combinations of wavelengths, power settings, and durations may provide good results as well.

Endoscopic Implementations

Figure 12:
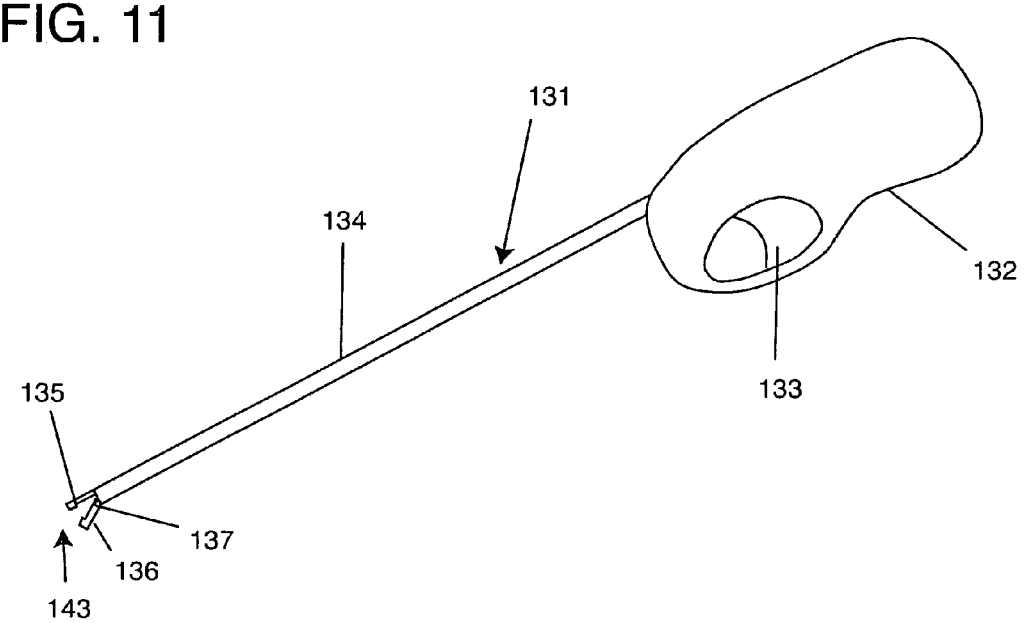
FIG. 12 is an isometric view of an implementation of a endoscopic laser tissue fusion device.

FIG. 12 depicts an implementation of a laser fusion device 131 suitable for endoscopic, or minimally invasive, procedures where the instrument operates through a tubular port to gain access to tissues within hollow organs or cavities, the abdomen, the thoracic cavity, and joints. These procedures have various labels, depending upon the location or organ in which the procedure is performed, including endoscopy, laparoscopy, thoracoscopy, arthroscopy, and others. The handle 132 and trigger 133 operate in ways similar to the implementations described above, but now the laser energy pathway, e.g., through a fiber optic cable, transmits the laser energy from an external source or diode mounted in the handle 132 to the distal end 143 through an extended, typically 20 cm to 50 cm, sheath or tube 134. The tissue to be affected is pinched between a static jaw 135 and a movable jaw 136, which pivots about hinge 137 when the trigger 133 is actuated.

Figure 13:
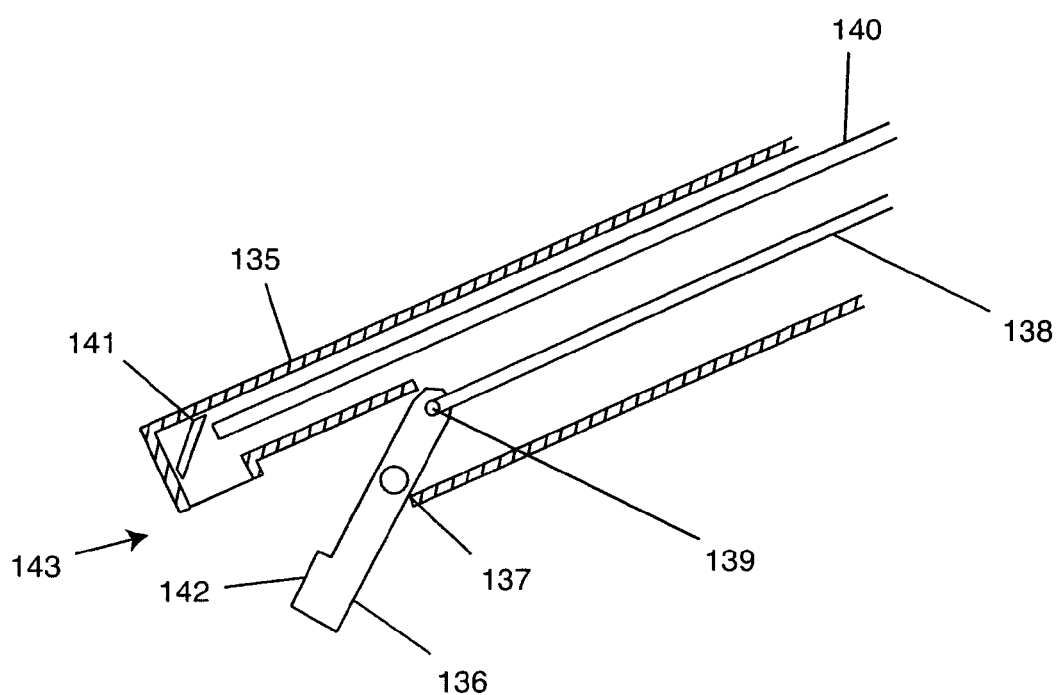
FIG. 13 is an elevation view in cross section of a detail of the distal tip of the endoscopic laser tissue fusion device of FIG. 12 in an open, pre-actuated state.

FIG. 13 depicts an enlarged view of the distal end 143 of the laser fusion device 131 for endoscopic procedures. Actuation of the trigger 133 causes translation of a tension cable 138, which is attached to the movable jaw 136 at a second hinge 139 and which causes the movable jaw 136 to rotate against the force of a rotational spring (not shown) about the hinge 137 that normally holds the movable jaw 136 in an open position. Thus, upon actuation of the trigger 133, any tissue located between the static jaw 135 and the movable jaw 136 will be held fast while the laser is on.

Laser energy from a laser energy source (not shown) is also activated upon actuation of the trigger 133 and is transmitted through a fiber optic cable 140. The laser light emanates from the distal end 143 of the static jaw 135 and is reflected towards the tissue held between the jaws 135, 136 by an angled reflector 141. The laser fires for a predetermined amount of time and at a predetermined energy level when the trigger 133 is actuated. The movable arm 136 may further be configured with a reflecting surface 142 at its distal end 143. The reflecting surface 142 may prevent any laser energy that penetrates the tissue entirely from irradiating undesired tissue locations by reflecting the laser energy back to the same tissue location receiving the incident laser energy.

Although various embodiments of this invention have been described above with a certain degree of particularity, or with reference to one or more individual embodiments, those skilled in the art could make numerous alterations to the disclosed embodiments without departing from the spirit or scope of this invention. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A device for laser fusion of biological tissue comprising
a first arm with a distal end;
a second arm with a distal end, wherein the distal end of the second arm is disposed opposite the distal end of the first arm;
a laser energy source that generates therapeutic laser energy;
an energy pathway that transmits the therapeutic laser energy from the laser energy source to the distal end of the first arm to deliver the therapeutic laser energy to layers of tissue of a patient positioned between the distal end of the first arm and the distal end of the second arm; and
an actuator configured to decrease a separation distance between the distal end of the first arm and the distal end of the second arm and further configured to activate the laser energy source.

2. The device of claim 1, wherein the actuator is further configured to deactivate the laser energy source.

3. The device of claim 1, wherein the energy pathway further comprises an optical fiber connected to the laser energy source.

4. The device of claim 1, wherein the distal end of the first arm comprises a reflector within the energy pathway to direct the therapeutic laser energy from the energy pathway to the layers of tissue.

5. The device of claim 1, wherein the distal end of the second arm further comprises a reflective surface positioned to reflect any of the therapeutic laser energy that travels through the tissue layers back into the tissue layers.

6. The device of claim 1, wherein
the distal end of the first arm is static; and
the distal end of the second arm is motile.

7. The device of claim 1 further comprising
a handle portion connected to the first arm and the second arm, and wherein
the laser energy source is positioned within the handle portion.

8. The device of claim 1 further comprising
a handle portion connected to the first arm and the second arm and housing the actuator;

a cable connected between the actuator and the laser energy source to transmit control instructions from the actuator to the laser energy source, wherein the laser energy source is positioned external to the handle portion.

9. The device of claim 1, wherein, upon actuation of the actuator, the distal ends of the first arm and the second arm apply pressure to the layers of tissue.

10. A device for laser septal fusion comprising
a first arm with a distal end configured for insertion into a first nostril of a patient;
a second arm with a distal end configured for insertion into a second nostril of a patient, wherein the distal end of the second arm is disposed opposite the distal end of the first arm;
a laser energy source that generates therapeutic laser energy;
an energy pathway that transmits the therapeutic laser energy from the laser energy source to the distal end of the first arm to deliver the therapeutic laser energy to septal tissue between the nostrils of the patient; and
an actuator configured to decrease a separation distance between the distal end of the first arm and the distal end of the second arm and further configured to activate the laser energy source.

11. The device of claim 10, wherein the actuator is further configured to deactivate the laser energy source.

12. The device of claim 10, wherein the energy pathway further comprises an optical fiber connected to the laser energy source.

13. The device of claim 10, wherein the distal end of the first arm comprises a reflector within the energy pathway to direct the therapeutic laser energy from the energy pathway to the layers of tissue.

14. The device of claim 10, wherein the distal end of the second arm further comprises a reflective surface positioned to reflect any of the therapeutic laser energy that travels through the tissue layers back into the tissue layers.

15. The device of claim 10, wherein
the distal end of the first arm is static; and
the distal end of the second arm is motile.

16. The device of claim 10 further comprising
a handle portion connected to the first arm and the second arm, and wherein
the laser energy source is positioned within the handle portion.

17. The device of claim 10 further comprising
a handle portion connected to the first arm and the second arm and housing the actuator;
a cable connected between the actuator and the laser energy source to transmit control instructions from the actuator to the laser energy source, wherein the laser energy source is positioned external to the handle portion.

18. The device of claim 10, wherein, upon actuation of the actuator, the distal ends of the first arm and the second arm apply pressure to the layers of tissue.

19. A method performing coaptation of nasal septal tissue comprising
pressing septal tissue together from opposite sides accessed through the nostrils of a patient;
applying therapeutic laser energy to the septal tissue for a period of time sufficient to fuse the septal tissue; and
releasing the pressure on the septal tissue.

20. The method of claim 19, wherein the applying operation further comprises applying the therapeutic laser energy to multiple small areas of the septal tissue.

21. A device for endoscopic laser tissue fusion comprising
a endoscopic tube;
a first jaw positioned at a distal end of the endoscopic tube;
a second jaw positioned at the distal end of the endoscopic tube and disposed opposite the first jaw;
a laser energy source that generates therapeutic laser energy;
an energy pathway that transmits the therapeutic laser energy from the laser energy source to the first jaw to deliver the therapeutic laser energy to layers of tissue of a patient positioned between the first jaw and the second jaw; and
an actuator configured to decrease a separation distance between a distal end of the first jaw and a distal end of the second jaw and further configured to activate the laser energy source.

22. The device of claim 21, wherein the actuator is further configured to deactivate the laser energy source.

23. The device of claim 21, wherein the energy pathway further comprises an optical fiber connected to the laser energy source.

24. The device of claim 21, wherein a distal end of the first jaw comprises a reflector within the energy pathway to direct the therapeutic laser energy from the energy pathway to the layers of tissue.

25. The device of claim 21, wherein a distal end of the second jaw further comprises a reflective surface positioned to reflect any of the therapeutic laser energy that travels through the tissue layers back into the tissue layers.

26. The device of claim 21, wherein
the first jaw is static; and
the second jaw is motile.

27. The device of claim 26 further comprising
a tension cable connected at a first end to the actuator and at a second end to the second jaw and which is placed under tension upon actuation of the actuator; and wherein
the second jaw further comprises a pivot structure fixed with respect to the endoscopic tube and about which the second jaw rotates when the tension cable is placed under tension to decrease the separation distance between the first jaw and the second jaw.

28. The device of claim 21 further comprising
a handle portion connected to the endoscopic tube, and wherein
the laser energy source is positioned within the handle portion.

29. The device of claim 21 further comprising
a handle portion connected to the endoscopic tube and housing the actuator;
a cable connected between the actuator and the laser energy source to transmit control instructions from the actuator to the laser energy source, wherein the laser energy source is positioned external to the handle portion.

30. The device of claim 21, wherein, upon actuation of the actuator, the distal ends of the first jaw and the second jaw apply pressure to the layers of tissue.

* * * * *